United States Patent [19]

Schnabel et al.

[11] 4,035,318

[45] July 12, 1977

[54] HIGH RESILIENCE POLYURETHANE FOAM

[75] Inventors: Wilhelm J. Schnabel, Branford; Ralph A. Colafati, III, New Haven, both of Conn.

[73] Assignee: Olin Corporation, New Haven, Conn.

[21] Appl. No.: 659,302

[22] Filed: Feb. 19, 1976

Related U.S. Application Data

[62] Division of Ser. No. 540,048, Jan. 10, 1975, Pat. No. 3,952,043, which is a division of Ser. No. 416,043, Nov. 15, 1973, Pat. No. 3,904,666.

[51] Int. Cl.² .................................... C08G 18/77
[52] U.S. Cl. ................................... 260/2.5 AT
[58] Field of Search ......................... 260/2.5 AT

[56] References Cited

U.S. PATENT DOCUMENTS

| 3,878,235 | 4/1975 | Schnabel | 260/2.5 AT |
|---|---|---|---|
| 3,880,780 | 4/1975 | Ridenour | 260/2.5 AT |
| 3,903,124 | 9/1975 | Schnabel | 260/2.5 AT |
| 3,904,666 | 9/1975 | Schnabel | 260/2.5 AT |
| 3,933,701 | 1/1976 | Puig | 260/2.5 AT |
| 3,939,124 | 2/1976 | DiBella | 260/2.5 AT |
| 3,952,043 | 4/1976 | Schnabel | 260/2.5 AT |
| 3,972,910 | 8/1976 | Metzger | 260/2.5 AT |
| 3,988,269 | 10/1976 | Puig | 260/2.5 AT |
| 3,993,610 | 11/1976 | Schnabel | 260/2.5 AT |

*Primary Examiner*—C. Warren Ivy
*Attorney, Agent, or Firm*—F. A. Iskander; T. P. O'Day

[57] ABSTRACT

Selected tetrafunctional methylene-bridged aromatic isocyanates and a method for their preparation are disclosed. The utility of these isocyanates as cross-linking agents for polyurethanes is also disclosed.

9 Claims, No Drawings

HIGH RESILIENCE POLYURETHANE FOAM

This is a division of application Ser. No. 450,048, filed Jan. 10, 1975, now U.S. Pat. No. 3,952,043, which in turn is a division of application Ser. No. 416,043, filed Nov. 15, 1973 and now U.S. Pat. No. 3,904,666, issued Sept. 9, 1975.

This invention relates to a select group of tetrafunctional methylene-bridged aromatic isocyanates and to a method for preparing them. The invention also relates to the use of these tetrafunctional isocyanates as cross-linking agents in the production of polyurethanes.

A variety of aromatic polyisocyanates has been known in the art. These include for example toluene diisocyanate and the polymeric isocyanates, e.g., polyphenylene polymethylene isocyanate, both of which have been used extensively in the production of polyurethane foam. A further group of such isocyanates is disclosed in U.S. Pat. No. 3,255,226 which relates to a Friedel-Crafts catalyzed condensation reaction involving an aromatic isocyanate having a haloalkyl substituent and selected substituted benzenes. This patent also indicates that in this type of reaction, a small portion of the specified substituted benzenes may condense with two moles of the haloalkyl-substituted aromatic isocyanate.

In the general art of polyurethane foam production, it is known that high resilience flexible foams can be prepared from a reaction mixture comprising selected high-molecular-weight polyols and preferably specified mixtures of toluene diisocyanate and polymeric polyisocyanate. It is also known in this particular art to include certain curing agents in the foam forming reaction mixture. The desirability of using a curing agent stems from the fact that, along with accelerating the curing rate of the foam, it also enhances its physical properties.

To date, the most commonly used curing agents have been the aromatic diamines, particularly the chlorinated aromatic diamines. However, due to their high degree of toxicitiy, these curing agents have become highly undesirable from an ecological standpoint. In fact, recent federal government regulations have prohibited or restricted the use of several of the most prominent such curing agents. Thus a need exists in the art for new curing agents which, while having reduced or no toxicity, can serve as viable substituents for the chlorinated aromatic diamines.

Now, in accordance with the invention, a new curing agent has been found which is identified as bis(-diisocyanatobenzyl)-chlorobenzene. This novel compound of the invention, along with being practically non-toxic, has been found to be a highly effective curing agent in the production of polyurethanes, particularly high resilience polyurethane foam. Further according to the invention, a selective process has been found for the optimized production of bis(-diisocyanatobenzyl)-chlorobenzene.

The novel compound of the invention can be a single isomer or a mixture of isomers represented by formula I as follows

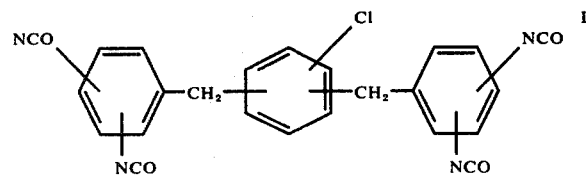

It is prepared, according to the method of the invention, by condensing, in the presence of a Friedel-Crafts catalyst, two moles of α-chloro-toluene diisocyanate with one mole of monochlorobenzene. In the course of this reaction, a substantial proportion of the α-chloro-toluene diisocyanate condenses with the monochlorobenzene in a 1:1 molar ratio to form diisocyanateophenyl-chlorophenyl-methane. Thus, as illustrated by the following reaction scheme, the product of the condensation of α-chloro-toluene diisocyanate with monochlorobenzene comprises, along with evolved hydrogen chloride, a mixture of two isocyanates:

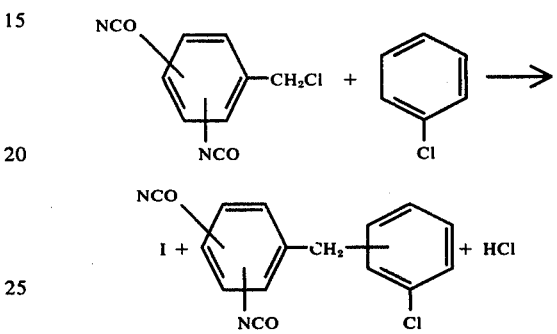

In carrying out the above-illustrated condensation reaction, any α-chloro-toluene diisocyanate isomer, or mixture of isomers, may be employed. Illustrative are α-chloro-2,4-toluene diisocyanate, α-chloro-2,6-toluene diisocyanate, α-chloro-2,5-toluene diisocyanate, α-chloro-3,5-toluene diisocyanate, and mixtures thereof. However, for reasons of economy and commercial availability, it is preferred to employ α-chloro-2,4-toluene diisocyanate, α-chloro-2,6-toluene diisocyanate or a mixture thereof. The latter is most preferred particularly the mixture of about 80% by weight of α-chloro-2,4-toluene diisocyanate and about 20% of α-chloro-2,6-toluene diisocyanate.

Any Friedel-Crafts type catalyst may be employed in carrying out the condensation reaction. This includes, for example, aluminum chloride, ferric chloride, zinc chloride, stannic chloride, and the like, aluminum chloride and ferric chloride being preferred. The catalyst may be used in any suitable proportion, such as from about 0.1 to about 4, and preferably about 0.4–2, parts per every 100 parts by weight of total reactants which are employed in preparing the bis(diisocyanatobenzyl)-chlorobenzene.

Any molar ratio of monochlorobenzene to α-chloro-toluene diisocyanate may be employed. However, it is preferred to employ the minimum possible number of moles of monochlorobenzene per each nmole of the α-chloro-toluene diisocyanate. This is in order to maximize the yield of bis(diisocyanatobenzyl)-chlorobenzene and correspondingly reduce the yield of diisocyanatophenyl-chlorophenyl-methane. Thus preferably no more than about 10 moles, and more preferably at most 5 moles, of the monochlorobenzene are employed per mole of the α-chloro-toluene diisocyanate. Furthermore, pursuant to the most preferred embodiments of the invention, from about 1.8 to about 4 moles of the monochlorobenzene are employed per mole of the α-chloro-toluene diisocyanate.

The condensation reaction is usually carried out at any suitable temperature provided this is below the temperature at which the reaction product undergoes decomposition or which temperature will result in undesirable boil-up of the reactive mixture. Thus at atmospheric pressure a reaction temperature of about 50°–135° C, and preferably about 90°–130° C, is used. The reaction is usually completed in about 1–12 hours as evidenced by the cessation of by-product HCl evolution. At this point, the excess monochlorobenzene is removed by distillation. The aluminum chloride is precipitated out by any suitable method, and it is removed by filtration along with any other solid matter that may be present. The remaining product will be a liquid blend or solution of bis(diisocyanatobenzyl)-chlorobenzene and diisocyanatophenyl-chlorophenyl-methane. Separation of these two compounds and recovery of the bis(diisocyanatobenzyl)-chlorobenzene can then be achieved using conventional distillation methods.

However, in accordance with one preferred embodiment of the invention, the blend of bis(diisocyanatobenzyl)-chlorobenzene and diisocyanatophenyl-chlorophenyl-methane is not separated. Rather it is used as such thereby doing away with the costly separation operation; for, according to the invention, it has been found that the effectiveness of the bis(diisocyantobenzyl)-chlorobenzene, as a curing agent in polyurethanes, is not diminshed or adversely affected by the presence therewith of diisocyanatophenyl-chlorophenyl-methane. In fact, to the extent that it is a low-viscosity liquid, this diisocyanate is a desirable component which acts as a solvent for the bis(diisocyanatobenzyl)-chlorobenzene. Its presence therefore makes for easy processing and mixing of the bis(diisocyanatobenzyl)chlorobenzene with the polyurethane forming reaction mixture.

The method of the invention enables the preparation of bis(diisocyanatobenzyl)-chlorobenzene is unexpectedly high yields; for unlike other substituted benzens, monochlorobenzene, when reacted with α-chloro-toluene diisocyanate, has been found to yield a surprisingly high proportion of product representing the condensation of two moles of α-chloro-toluene diisocyanate with one mole of monochlorobenzene. As such, the method of the invention provides for optimum production of bis(diisocyanatobenzyl)-chlorobenzene via this type of condensation reaction.

This bis(diisocyanatobenzyl)-chlorobenzene of the invention is practically non-toxic and acts as an effective cross-linking agent in polyurethane compositions. It is of particular utility, according to the invention, as a cross-linking or curing agent for high resilience flexible polyurethane foams.

Any flexible polyurethane form which is characterized by high resilience properties may be ucred using the bis(diisocyanatobenzyl)-chlorobenzene curing agent of the invention. Usually such foams are prepared from a reaction mixture comprised of a select poluyether triol, an organic isocyanate, or blend of organic isocyanates, a foaming agent and a reaction catalyst. Either the one-shot method or the so-called "prepolymer technique" may be used in carrying out the foaming reaction although the one-shot method is preferred.

The select polyether triol which is used is characterized by (1) a molecular weight of at least about 4,400, (2) a trifunctional alcohol nucleus, (3) polyoxypropylene chain segments attached at one end thereof to the nucleus and (4) poyoxyethylene chain segments attached at one end thereof to the polyoxypropylene chain segments, with the proviso that the resulting polyether contains no less than about 7, and no more than about 18, moles of ethylene oxide per each mole of trifunctional alcohol. This polyether can be prepared by methods generally well known in the art wherein a trifunctional alcohol initiator is sequentially condensed, in the presence of an alkaline catalyst, first with propylene oxide and then with ethylene oxide.

The alcohol initiator used in preparing the polyether triol can be any compound having three hydroxyl terminal groups. However, the aliphatic triols are preferred, particularly those containing 3–12 carbons. Illustrative are glycerol, trimethylolpropane, triethylolpropane, 1,3,5-hexanetriol, 1,2,6-hexanetriol, 1,4,6-octanetriol, and 1,5,10-dodecane triol. In accordance with the most preferred embodiment of the invention, aliphatic triols having 3–6 carbon atoms are employed such as glycerol and trimethylolpropane.

While as indicated above any polyether triol, as described above, may be employed in preparing the polyurethane foams of the invention, it is preferred to use those polyether triols which have a molecular weight of about 5,700–7,000 and still preferably about 5,800–6,600. It is also preferred that the ethylene oxide content in the polyether triol range from about 12 to about 17, and more preferably from about 14 to about 16 moles per each mole of trifunctional alcohol.

In preparing the high resilience polyurethane foam, any suitable organic isocyanate or mixture of isocyanates may be used. It is preferred however to employ toluene diisocyanate, such as the 80/20 weight mixture of the 2,4-/2,6- isomers, or a selected mixture of toluene diisocyanate and a polymeric isocyanate such as the polyphenylene polymethylene isocyanates described in U.S. Pat. No. 2,683,730. The entire disclosure of this patent is incorporated by reference herein. Where a mixture of toluene diisocyanate and a polymeric isocyanate is used, this usually has a weight ratio, toluene diisocyanate:polymeric isocyanate, ranging from about 75:25 to about 96:4 and preferably from about 85:15 to about 94:6. In the most preferred embodiment of the invention, the weight ratio of toluene diisocyanate to the polymeric isocyanate ranges from at about 87:13 to about 92:8. The ratio of NCO to OH groups, in the foam forming reaction mixture, multiplied by 100 is referred to as the "index".

The amount of isocyanate reactant or mixture thereof that is employed to the exclusion of the curing agent generally be sufficient to provide at least 0.7 NCO group per hydroxyl group in the reaction system, which includes the polyether triol as well as any additional material and/or foaming agent present in the system. In practice such as proportion of isocyanate is employed as to provide no more than about 1.25, and preferably about 0.9–1.15 NCO groups per each hydroxyl group.

The polyurethane foams of the invention are prepared in the presence of bis(diisocyanatobenzyl)-chlorobenzene curing agent which is in addition to the isocynate reactant. While any suitable additive amount of this curing agent may be employed, it is preferred to employ relatively small amounts such as about 0.5–5.0 and preferably about 1–4.0, parts per 100 parts by weight of the polyether triol. This is in order to preclude any adverse effects which might result from using too much or too little curing agent. According to the most preferred embodiment of the invention, the curing agent is used in a proportion of about 1.6–2.4 parts per 100 parts by weight of the polyether triol.

As indicated above, it is preferred to employ the bis(diisocyanatobenzyl)-chlorobenzene as a mixture or solution thereof in diisocyanatophenyl-chlorophenyl-methane. Such use not only accomplishes a substantial saving in not having to separate these two materials which are simultaneously formed in the condensation of α-chloro-toluene diisocyanate with chlorobenzene, but it also provides the added advantage that, as such, the blend is a liquid material of low viscosity. Therefore, it is easier to process and admix with other foam forming reactants than is the bis(diisocyanatobenzyl)-chlorobenzene alone. Any such blend may be employed, provided it contains at least about 10% by weight of the bis(diisocyanatobenzyl)-chlorobenzene. However, as a matter of economy and convenience, it is preferred to employ the blends which are directly obtained from the reaction described above. Such blends, according to the invention, usually have a weight ratio, bis(diisocyanatobenzyl)-chlorobenzene:-diisocyanatophenyl-chlorophenyl-methane, ranging from about 15:85 to about 60:40, and preferably about 25:75 to about 50:50. Such blends have been found to be eminently suitable as cross-linking agents for flexible, high resilience polyether polyurethane foam.

Where a blend of bis(diisocyanatobenzyl)-chlorobenzene and diisocyanatophenyl-chlorophenyl-methane is used, a sufficient proportion thereof is employed as to provide the required amount of bis(-diisocyanatobenzyl)-chlorobenzene which is specified above.

In preparing the polyurethane foams of the invention any suitable foaming agent, or mixture of foaming agents, may be employed. These include inorganic foaming agents such as water and organic foaming agents containing up to seven carbon atoms such as the halogenated hydrocarbons and the low molecular weight alkanes, alkenes, and ethers. Illustrative organic foaming agents include monofluorotrichloromethane, dichlorofluoromethane, dichlorodifluoromethane, 1,1,2-trichloro-1,2,2-trifluoroethane, methylene chloride, chloroform, carbon tetrachloride, methane, ethane, ethylene, propylene, hexane, ethyl ether and diisopropyl ether. Water and the low molecular weight polyhalogenated alkanes, such as monofluorotrichloromethane and dichlorodifluoromethane, are preferred. The amount of foaming agent may be varied within a reasonable wide range as is well known in the art. Generally however, the halogenated alkanes, for example, are employed in an amount of about 2–20, parts per 100 parts by weight of the polyether triol which is used in making the foam; and water is employed in an amount of about 1–6, and preferably about 1.5–4.5, parts per 100 parts of polyether triol.

The polyurethane foams of the invention are prepared in the presence of a catalytic amount of a reaction catalyst. The catalyst employed may be any of the catalysts known to be useful for this purpose, or mixtures thereof, including tertiary amines and metallic salts, particularly stannous salts. Typical tertiary amines include, but are not limited to, the following: N-methyl morpholine, N-hydroxyl-ethyl morpholine, triethylene diamine, bis(2-dimethylaminoethyl)ether, triethylamine and trimethylamine. Typical metallic salts include, for example, the salts of antimony, tin and iron, e.g., dibutyltin dilaurate, stannous octoate, and the like. In accordance with a preferred embodiment of the invention, a catalyst comprised of an amine, such as triethylene diamine and a stannous salt, such as stannous octoate, is employed. Any catalytic proportion of catalysts may be employed, such as about 0.04 and about 1.5, and preferably between about 0.05 and about 0.75 percent weight based on the total weight of the polyether triol which is used in preparing the foam.

It is preferred in the preparation of the polyurethane foams of the invention to employ amine minor amounts of certain surfactants in order to further improve the cell structure of the polyurethane foam. Suitable such surfactants include the silicones and the siloxane-oxyalkylene block copolymers, all of which are commercially available materials. Generally up to 2 parts of the siloxane copolymer or up to 0.1 parts of the silicone are employed per every 100 parts by weight of the polyether triol.

In the practice of this invention, a polyurethane foam-forming reaction mixture comprising the above-described ingredients is fed to a suitable reaction zone such as by pouring into a suitable mold or onto a moving conveyor belt where reaction proceeds. The foaming reaction is exothermic, and auxiliary heat is usually not necessary to effect the reaction, although it may be employed. After the reactants have been admixed for a period of between about 0.1 to about 20 seconds, an emulsion or "cream" forms. As the temperature increases from the reaction, gas bubbles are generated bringing about the formation of an uncured cellular gel material which usually cures fairly rapidly at room temperature. Once cured, the foam will be ready for use in various cushioning applications.

Polyurethane foams prepared according to the process of the invention are characterized by a unique and highly desirable combination of physical properties. Ranging in density from about 1.8 to about 3.8, and preferably from about 2.2 to 3.0, pounds per cubic foot, they hvve a SAC factor generally in excess of 2.4 and usually at least 2.7. The "SAC factor" is a measure of support provided by a cushioning material. In accordance with the test described in ASTM D-1564-64T, it is expressed as the ratio of indentation load deflection, ILD, at 65 percent to 25 percent deflection. Thus by having a SAC factor of over 2.4, the foams of the invention, while being quite flexible and soft at the surface, exhibit little or no tendency to bottom out; and this property is achieved in the foams of the invention in the absence of fillers or other expedients which might alter the basic properties of the foam.

The polyurethane foams of the invention are also endowed with substantially the same desirable physical properties that characterize prior art high resilience polyurethane foams. For example, they have high ball drop resilience properties and improved tensile and tear strength. In addition, these foams exhibit relatively little change in physical properties when subjected to accelerated heat or humid aging.

Furthermore, foams prepared according to the invention are characterized by good elongation, tensile and tear strength, and high ball drop resilience, i.e., over 45 percent as determined by the test described in ASTM D-1564,-64T. They also exhibit a sufficient degree of resistance to burning such as to meet the requirements of the Motor Vehicle Safety Standard Test No. 302. This test is described in the Jan. 8, 1971 issue of *The*

*Federal Register*, Volume 36, No. 5, beginning on page 289.

By virtue of the combination of desirable physical properties characterizing the polyurethane foams of the invention, these foams meet the rigid requirement set by the automotive industry for making molded auto seats. They are also of utility in numerous other cushioning applications such as in the manufacture of padding, seat cushions and the like.

The following examples are provided to illustrate the invention. In these examples, all parts and percentages are by weight unless otherwise specified.

EXAMPLE 1

In a reaction vessel, equipped with a stirrer, a thermometer, a reflux condenser, a gas inlet tube and a dropping funnel, there were placed 1688.4 grams (15 moles) of monochlorobenzene and 6.7 grams of aluminum chloride. Then there were gradually added, over a period of about 2.5 hours, 626 grams (3 moles) of $\alpha$-chloro-toluene diisocyanate which consisted of 80% by weight $\alpha$-chloro-2,4-toluene diisocyanate and 20% $\alpha$-chloro-2,6-toluene diisocyanate. During the addition and until completion of the reaction, the temperature inside the reaction vessel was maintained within 120°–130° C and a slow stream of dry nitrogen gas was passed through the reaction mixture. The effluent nitrogen gas, which was laden with evolved HCl was passed into a water vessel where the HCl was captured by absorption and eventually total evolved HCl was determined by titration with base. In the course of the reaction, an additional amount of 13.4 grams aluminum chloride was added.

Upon completion of the reaction, as evidenced by the cessation of HCl evolution, substantially all of the excess monochlorobenzene was removed by vacuum distillation. The remaining reaction product mixture was analyzed by gel permeation chromatography (GPC). The chromatogram showed two sharp peaks and some tailing. The positions of the peaks, compared to a calibration curve, and computer integration of the peak areas indicated that the reaction product contained (1) difunctional diisocyanatophenyl-chlorophenyl-methane and (2) tetrafunctional bis(diisocyanatobenzyl)-chlorobenzene, in a weight ratio, (1):(2), of 68.6:31.4. The product was a liquid, stable for several months, having a surprisingly low viscosity, at 25° C, of 216 cps.

EXAMPLES 2–5

The identical procedure of Example 1 was followed in carrying out these examples except that different and varying proportions of the monochlorobenzene were used such as to provide a molar ratio, monochlorbenzene:$\alpha$-chloro-toluene diisocyanate, which varied from 10:1 to 2:1. In the case of each of these examples, the reaction product was found to contain a mixture of diisocyanatophenyl-chlorophenyl-methane and bis(diisocyanatophenyl)-chlorobenzene. The molar ratios of reactants and the constitution of the product is given in Table I below.

COMPARISONS 1–5

The identical procedure of Examples 1–5 was repeated, except that instead of the chlorobenzene reactant, isocyanatobenzene was used. The product of each of these comparisons was shown by GPC to be a mixture of diisocyanatophenyl-isocyanatophenyl-methane and bis(diisocyanatobenzyl)-isocyanatobenzene. The molar ratios of reactants used in these comparisons and the compositions of the resulting products are provided in Table I below.

TABLE I

| | Condensation Reactions Involving $\alpha$-Chloro-TDI & Substituted Benzenes | | | |
|---|---|---|---|---|
| | Reactants Data | | Product Analysis(grams) | |
| | Substituted Benzene Used | Molar Ratio[1] | 1:1 Mole Condensate[2] | 2:1 Mole Condensate[3] |
| Example 1 | chlorobenzene | 5:1 | 68.6 | 31.4 |
| Comparison 1 | isocyanatobenzene | 5:1 | 84.1 | 15.9 |
| Example 2 | chlorobenzene | 10:1 | 78.0 | 22.0 |
| Comparison 2 | isocyanatobenzene | 10:1 | 92.3 | 7.7 |
| Example 3 | chlorobenzene | 4:1 | 64.3 | 35.7 |
| Comparison 3 | isocyanatobenzene | 4:1 | 81.1 | 18.9 |
| Example 4 | chlorobenzene | 3:1 | 58.5 | 41.5 |
| Comparison 4 | isocyanatobenzene | 3:1 | 76.8 | 23.2 |
| Example 5 | chlorobenzene | 2:1 | 49.1 | 50.9 |
| Comparison 5 | isocyanatobenzene | 2:1 | 69.2 | 30.8 |

[1] Molar ratio of substituted benzene to $\alpha$-chloro-TDI used.
[2] In the case of each of Examples 1-5, this condensate is diisocyanatophenyl-chlorophenyl-methane; and in the case of each of Comparisons 1-5, this condensate is diisocyanatophenyl-isocyanatophenyl-methane.
[3] In the case of each of Examples 1-5, this condensate is bis(diisocyanatobenzyl)chlorobenzene; and in the case of each of Comparisons 1-5, this condensate is bis(diisocyanatobenzyl)-isocyanatobenzene.

The data in Table I demonstrates the unexpectedly high tendency of monochlorobenzene to condense with two moles of $\alpha$-chloro-toluene diisocyanate as compared with the same type of condensation reaction involving $\alpha$-chloro-toluene diisocyanate and another prior art substituted benzene, namely, isocyanatobenzene. Inasmuch as this result is shown to obtain at various levels of reactants molar ratio, it demonstrates the surprising improvement provided by the invention for preparing bis(diisocyanatobenzyl)-chlorobenzene.

COMPARISON 6

For further comparison purposes, Example 3 was repeated except that instead of the monochlorobenzene reactant, toluene was used. The product was confirmed by GPC to be a mixture of 86.1% by weight of diisocyanatophenyl-methylphenyl-methane and 13.9% by weight of bis(diisocyanatobenzyl)-toluene.

EXAMPLE 6

The amount of 7.5 grams of the product of Example 1 (which is equivalent of 2.36 grams of the bis(diisocyanatobenzyl)-chlorobenzene of the invention) was used as a curing agent in preparing a flexible polyurethane foam from the following ingredients in the indicated proportions:

| Ingredients | Grams |
| --- | --- |
| Polyether triol[1] | 100.0 |
| Water | 3.1 |
| Catalyst system | |
| triethylene diamine [2] | 0.4 |
| bis(2-dimethylaminoethyl)ether [3] | 0.04 |
| stannous octoate | 0.02 |
| Polymethylsiloxane surfactant [4] | 0.04 |
| Toluene diisocyanate (80/20 mixture of 2,4-/2,6-isomers), index | 105 |

[1]This is a 6,500 molecular-weight polyether triol prepared by sequentially oxyalkylating glycerin first with about 98 moles of propylene oxide and then with about 15 moles of ethylene oxide. [2]Purchased commercially under the trademark "Dabco 33-LV". [3]Purchased commercially under the trademark "Niax A-1". [4]Purchased commercially under the trademark "DC-200-5".

The above mixture, including the 7.5 grams of the product of Example 1, was hand-mixed at room temperature and immediately poured into a square aluminum mold which had been pre-heated to about 60° C. Foaming took place instantaneously and was completed in about 2.5 minutes. After the lapse of 15 minutes from the time that the mixture was placed into the mold, the foam had acquired a wholesome body which could be removed from the mold free of surface defects. The foam was subjected to various tests in order to determine its physical properties. The results of these tests are provided in Table II below.

COMPARISON 7

The identical procedure of Example 6 was followed with two exceptions. First instead of utilizing the curing agent of the invention, a prior art curing agent was used, namely 2.5 grams of a chlorinated diamino dephenyl methane composition purchased commercially under the trademark "Curene 126". Secondly, instead of the straight toluene diisocyanate reactant, a prior art isocyanate mixture was used which is known to be a necessary ingredient in making high resilience polyurethane foam. This isocyanate mixture consisted of 80% by weight of toluene diisocyanate (80/20 mixture of 2,4-/2,6- isomers) and 20% of polyphenylene polymethylene isocyanate sold commercially under the trademark "PAPI". Again the physical properties of this foam were tested and the results are given in Table II.

Table II

| | Example 6 | Comparison 7 |
| --- | --- | --- |
| Core density(lbs. per cu.ft.) | 2.5 | 2.6 |
| Indentation load deflection(lbs.), per ASTM D-1564-64T | | |
| a) at 25% deflection | 38 | 34 |
| b) at 65% deflection | 97 | 108 |
| c) SAC factor(b÷a) | 2.5 | 3.1 |
| Ball rebound, %, per ASTM D-1564-64T | 54 | 54 |
| Tensile strength(lbs.per sq.in.) | 17.8 | 21 |
| Tear strength(lbs.per linear foot) | 3.6 | 2.6 |

The data in Table II demonstrates the effectiveness of the curing agent of the invention as compared with a prior art curing agent. As shown, the invention foam and the prior foam are both high resilience with substantially comparably desirable properties. It is also to be noted that the high resilience properties of the foam of the invention obtain even though no polymeric isocyanate was used in making this foam as distinguished from the prior art foam.

What is claimed is:

1. A flexible, high resilience polyurethane foam which is prepared from a reaction mixture comprising an organic polyisocyanate reactant, a polyol reactant, a foaming agent, a reaction catalyst, and, as a curing agent, addition to said organic isocyanate reactant bis(diisocyanatobenzyl)-chlorobenzene.

2. The polyurethane foam of claim 1 wherein said curing agent is comprised of said bis(diisocyanatobenzyl)-chlorobenzene and diisocyanatophenyl-chlorophenyl-methane, the weight ratio of bis(-diisocyanatobenzyl)-chlorobenzene to diisocyanatophenyl-chlorophenyl-methane ranging from about 15:85 to about 60:40.

3. The polyurethane foam of claim 2 wherein said polyol is an oxypropylated, oxyethylated triol characterized by (a) a molecular weight of at least about 4,400, (b) a trifunctional alcohol nucleus, (c) polyoxypropylene chain segments attached at one end thereof to said nucleus, (d) polyoxyethylene chain segments attached at one end thereof to said polyoxypropylene chain segments, and (e) from about 7 to about 18 moles of ethylene oxide per each mole of said trifunctional alcohol.

4. The polyurethane foam of claim 3 wherein said organic polyisocyanate is toluene diisocyanaate or a mixture thereof with polyphenylene polymethylene isocyanate, said mixture having a weight ratio, of toluene diisocyanate to polyphenylene polymethylene isocyanate, ranging from about 85:15 to about 94:6.

5. The polyurethane foam of claim 4 wherein said weight ratio of bis(diisocyanatobenzyl)-chlorobenzene to diisocyanatophenyl-chlorophenyl-methane ranges from about 25:75 to about 50:50.

6. The polyurethane foam of claim 5 wherein said oxypropylated, oxyethylated triol has a molecular weight of about 5,700–7,000 and contains about 12–17 moles of ethylene oxide per each mole of said trifunctional alcohol.

7. The polyurethane foam of claim 6 wherein said reaction mixture comprises a surfactant and said foaming agent is water.

8. The polyurethane foam of claim 7 wherein said catalyst comprises a tertiary amine and a stannous salt.

9. The polyurethane foam of claim 8 wherein said oxypropylated, oxyethylated triol has a glycerin nucleus, a molecular weight of about 5,800–6,600 and contains about 12–17 moles of ethylene oxide per mole of glycerin.

* * * * *

UNITED STATES PATENT OFFICE
CERTIFICATE OF CORRECTION

Patent No. 4,035,318  Dated July 12, 1977

Inventor(s) Wilhelm J. Schnabel and Ralph A. Colafati, III

It is certified that error appears in the above-identified patent and that said Letters Patent are hereby corrected as shown below:

Column 1, Line 47, delete the word "substituents" and insert therefor --substitutes--.

Column 2, Line 56, delete "nmole" and insert therefor --mole--.

Column 3, Line 39, delete the word "is" and insert therefor --in--.

Column 3, Line 40, delete "benzens" and insert therefor --benzenes--.

Column 3, Line 49, delete the word "This" and insert therefor --The--.

Column 3, Line 55, delete the word "form" and insert therefor --foam--.

Column 3, Line 56, delete "ucred" and insert therefor --cured--.

Column 3, Line 60, delete "poluyether" and insert therefor --polyether--.

Column 4, Line 2, delete "poyoxyethylene" and insert therefor --polyoxyethylene--.

Column 4, Line 26, after the word "still" add the word --more--.

Column 4, Line 52, after the word "agent" add the word --should--.

Column 4, Line 56, delete the word "as" and insert therefor --a--.

Column 6, Line 8, after the word "percent", insert the word --by--.

UNITED STATES PATENT OFFICE
CERTIFICATE OF CORRECTION

Patent No. 4,035,318      Dated July 12, 1977

Inventor(s) Wilhelm J. Schnabel and Ralph A. Colafati, III

It is certified that error appears in the above-identified patent and that said Letters Patent are hereby corrected as shown below:

Column 6, Line 11, delete the word "amine".

Column 6, Line 29, delete the word "to" and insert therefor --and--.

Column 6, Line 39, after the word "to" add the word --about--.

Column 6, Line 40, delete "hvve" and insert therefor --have--.

Column 6, Line 65, after "D-1564" delete the comma.

Column 8, Example 6, Line 64, delete the word "of", first appearance, and insert therefor --to--.

Column 9, Comparison 7, Line 34, delete "dephenyl" and insert the word --diphenyl--.

Column 10, Line 3, delete the word "comparably" and insert therefor --comparable--.

Column 10, Claim 1, Line 13, after the word "agent," add the word --in--.

Signed and Sealed this

Twenty-first Day of February 1978

[SEAL]

Attest:

RUTH C. MASON
*Attesting Officer*

LUTRELLE F. PARKER
*Acting Commissioner of Patents and Trademarks*